(12) United States Patent
Shelso et al.

(10) Patent No.: US 8,221,387 B2
(45) Date of Patent: Jul. 17, 2012

(54) CATHETER HAVING AN IMPROVED DISTAL TIP

(75) Inventors: Susan Shelso, Plymouth, MN (US); Andrzej Malewicz, Minneapolis, MN (US); John R. Moberg, Elk River, MN (US)

(73) Assignee: Boston Scientific Scimed, Inc., Maple Grove (*) Notice: Subject to any disclaimer, the term of this patent is extended or adjusted under 35 U.S.C. 154(b) by 1585 days.

(21) Appl. No.: 10/785,348

(22) Filed: Feb. 24, 2004

(65) Prior Publication Data

US 2005/0187536 A1    Aug. 25, 2005

(51) Int. Cl.
*A61M 25/00* (2006.01)

(52) U.S. Cl. ............... 604/523; 604/164.13; 604/164.01

(58) Field of Classification Search ............... 604/96.01, 604/246, 247, 249, 256, 264, 537, 912, 915, 604/523–532, 164.01, 164.13, 170.01, 170.02, 604/294

See application file for complete search history.

(56) References Cited

U.S. PATENT DOCUMENTS

| | | | |
|---|---|---|---|
| 4,531,943 A * | 7/1985 | Van Tassel et al. | 604/523 |
| 4,738,659 A * | 4/1988 | Sleiman | 604/103.09 |
| 5,078,702 A | 1/1992 | Pomeranz | |
| 5,316,706 A * | 5/1994 | Muni et al. | 264/472 |
| 5,549,580 A | 8/1996 | Diaz | |
| 5,643,209 A | 7/1997 | Fugoso et al. | |
| 5,766,160 A | 6/1998 | Samson et al. | |
| 5,772,669 A | 6/1998 | Vrba | |
| 5,827,225 A | 10/1998 | Ma Schwab | |
| 5,860,963 A | 1/1999 | Azam et al. | |
| 5,865,800 A | 2/1999 | Mirarchi et al. | |
| 5,989,208 A * | 11/1999 | Nita | 604/22 |
| 6,059,770 A | 5/2000 | Peacock, III et al. | |
| 6,080,170 A * | 6/2000 | Nash et al. | 606/159 |
| 6,168,570 B1 | 1/2001 | Ferrera | |
| 6,190,393 B1 | 2/2001 | Bevier et al. | |
| 6,224,610 B1 | 5/2001 | Ferrera | |
| 6,679,903 B2 | 1/2004 | Kurz | |
| 2003/0125751 A1 * | 7/2003 | Griffin et al. | 606/108 |
| 2004/0015138 A1 | 1/2004 | Currier et al. | |

FOREIGN PATENT DOCUMENTS

DE    33 26 648 A1    2/1985
DE    34 02 573 A1    8/1985

* cited by examiner

*Primary Examiner* — Jackie Ho
*Assistant Examiner* — Laura Schell
(74) *Attorney, Agent, or Firm* — Seager, Tufte & Wickhem LLC

(57) ABSTRACT

One embodiment is a medical device comprising an elongate catheter having a proximal end, a distal end, and a lumen extending therethrough and a tip disposed at the distal end of the elongate catheter, the tip extending distally of the distal end of the catheter, the tip comprising a soft body portion and a rigid ring distal the soft body portion.

12 Claims, 4 Drawing Sheets

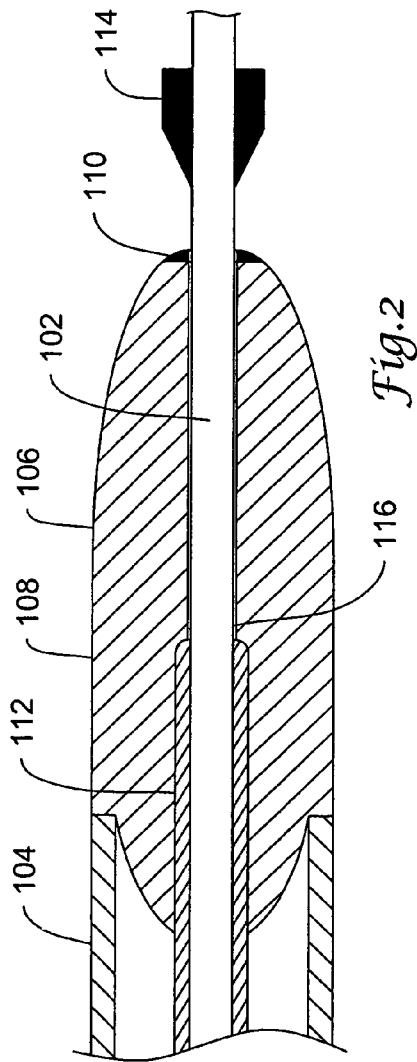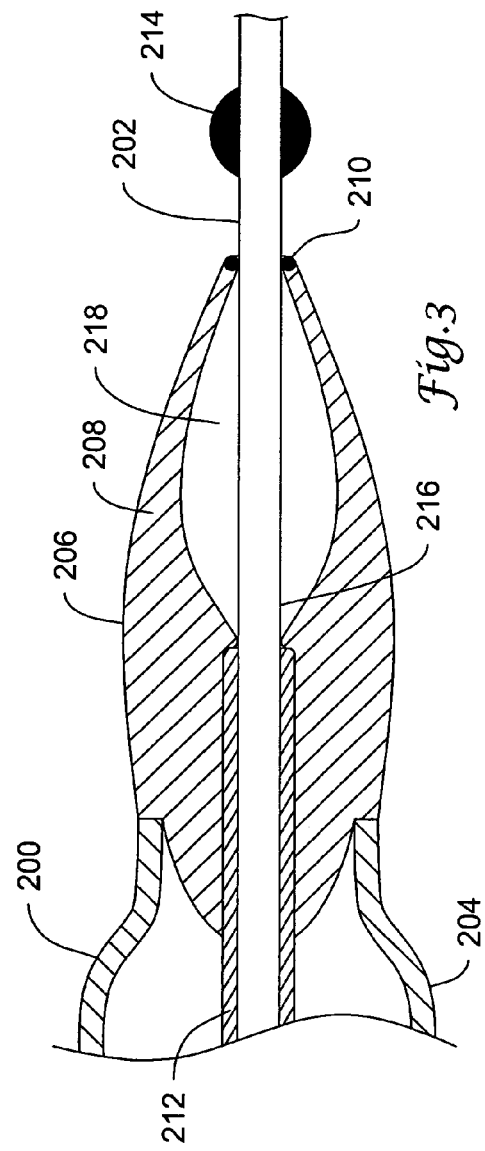

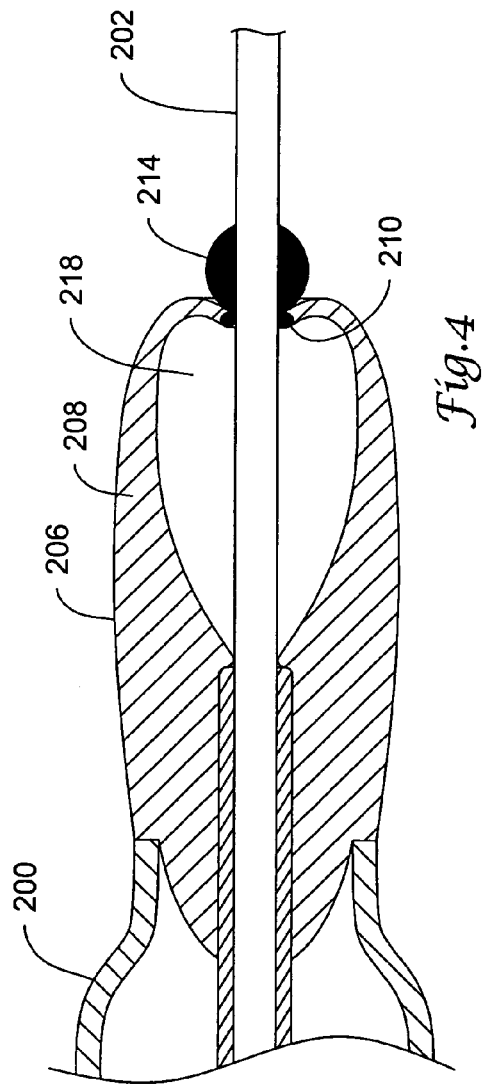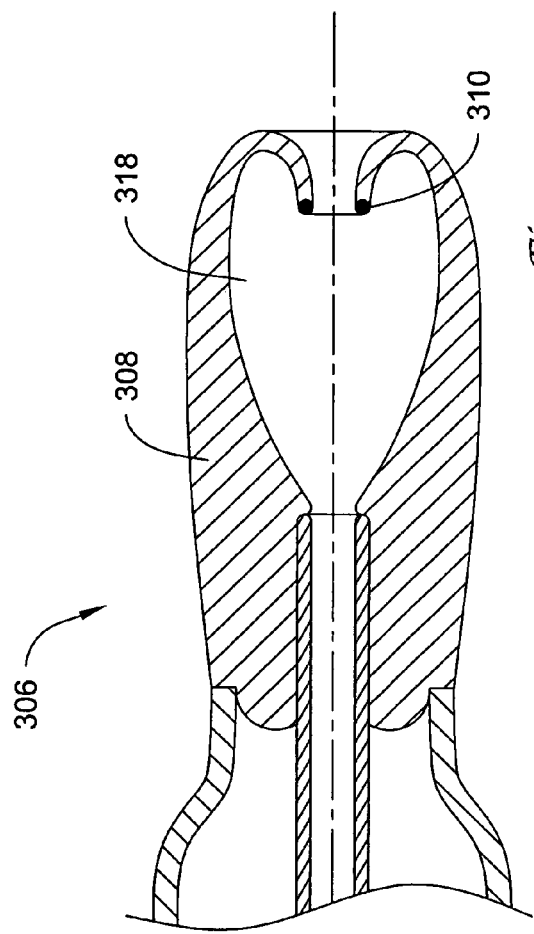

United States Patent US 8,221,387 B2

CATHETER HAVING AN IMPROVED DISTAL TIP

FIELD

The present invention generally relates to intravascular medical devices. More particularly, the present invention relates to intravascular catheters having an improved distal tip.

BACKGROUND

Diagnostic catheters and guide catheters are commonly used to facilitate the diagnosis and treatment of vascular diseases such as coronary artery disease and peripheral vascular disease. Balloon catheters are commonly used to treat vascular disease by dilating stenotic lesions. Treatment and diagnostic catheters and other medical devices are often advanced distally over a guidewire or a distal protection device having a stop. Often, the distal tips of medical devices such as catheters are soft and flexible to reduce trauma to vessel walls. However, if the catheter is used on a guidewire or other device that has a stop, the distal end of the medical device may ride up on or become engaged with the stop. There is an ongoing need to provide alternative designs and methods for making and using medical devices which alleviates this problem and still reduces potential trauma to vessel walls.

SUMMARY

In one example embodiment, a medical device has a distal tip having a radially non-extensible distal end. The medical device may be advanced over a guidewire or a distal protection device up to a stop with a reduced chance of the medical device lodging on the stop. The tip may include a flexible proximal portion which may cushion the medical device from the stop and may store energy to dislodge the medical device from the stop. The radially non-extensible end may include a molded or machined plastic or metal ring, a ring formed from deposition, a locally crystalline portion of an amorphous polymer, or other suitably strong and rigid material. It may, for example, be a wire ring or soldered coil. A proximal portion of the distal tip may be elastic to permit deformation yet strong enough to resist tearing. It may, for example, be made from a suitable polymer having a suitable configuration.

In another example embodiment, the distal tip may be formed to have a distally tapering shape with a lumen therethrough having an elongated distal portion. The distal tip may be formed to have a distally tapering shape which has a wall which thins more rapidly than the taper, creating a hollow in the distal lumen.

In yet another example embodiment, the distal tip may also be formed to have a preformed inverted portion as described below.

The above summary of some embodiments is not intended to describe each disclosed embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings in which:

FIG. 2 is a partial cross-sectional view of the example medical device of FIG. 1, the section line passing through the longitudinal axis.

FIG. 3 is a partial cross-sectional view of another example medical device, the section line passing through the longitudinal axis.

FIG. 4 is a cross-sectional view of the example medical device of FIG. 3, the section line passing through the longitudinal axis.

FIG. 5 is a cross-sectional view of an example medical device.

Figure 1:
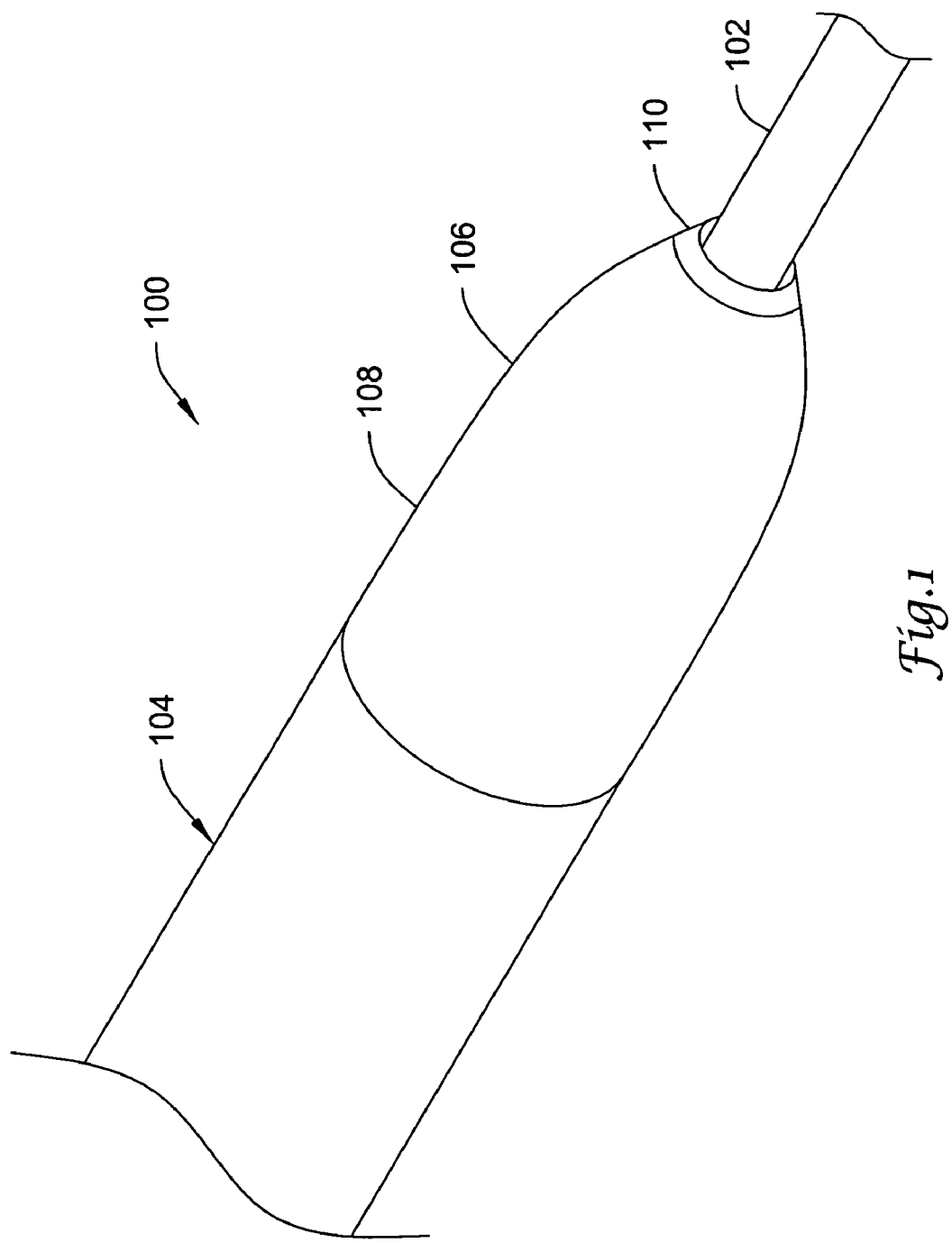
FIG. 1 is a partial perspective view of an example medical device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF EXAMPLE EMBODIMENTS

As used in this specification and the appended claims, the singular forms "a", "an", and "the" may include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates a partial perspective view depicting a medical device 100 disposed on a guidewire 102. By way of example and not limitation medical device 100 shown is a stent delivery catheter system. However, it is recognized that the invention is susceptible to other medical devices such as angioplasty catheters, guide cathethers, atherectomy devices, intravascular filters, interventional devices, and therapeutic agent delivery systems. This list is intended to be exemplary and not limiting. Medical device 100 includes a tubular member 104 and a distal tip 106. Medical devices having other components or configurations are contemplated. For example, tubular member 104 and distal tip 106 may be integral, or one or both may be formed separately and then attached. Distal tip 106 includes a generally soft body portion 108 and a rigid annular ring 110.

Turning to FIG. 2, which shows a cross-sectional view of the embodiment of FIG. 1, medical device 100 may include other components such as inner tube 112 and has a lumen 116 extending therethrough. Ring 110 is radially relatively non-extensible. "Radially non-extensible" is intended to be broader than completely rigid and is intended to mean relatively non-compliant in the radial direction. Of course, if a ring is completely rigid, it is also radially non-extensible. Thus, if medical device 100 is advanced distally up guidewire 102 to a distal stop 114 on the guidewire, distal tip 106 will not ride up on or over distal stop 114 and thereby engage the distal stop. Instead, soft body portion 108 will absorb the energy and compress or deflect. Soft body portion 108 may release the stored energy by pushing the proximal portion of medical device 100 proximally until the stored energy is released. Thus, distal tip 106 may help to more precisely position medical device 100 relative to distal stop 114 by providing tactile feedback, for instance.

FIG. 3 shows a partial cross-sectional view of another example embodiment. A balloon catheter 200 is disposed on a guidewire 202 having a distal stop 214. Of course, a balloon catheter is merely an example medical device and other medical devices are contemplated. Balloon catheter 200 may have a balloon membrane 204, an inner tube 212, and a lumen 216 extending therethrough. Balloon catheter 200 also includes a distal tip 206 having a radially non-extensible ring 210 and a soft body portion 208. Distal tip 206 gradually tapers towards the distal end. This taper may be curved, as shown, may be linear, or may have steps, depending on the desired configuration.

Lumen 216 in distal tip 206 portion may also include a cavity 218. Cavity 218 may help increase the flexibility of soft body portion 208 by reducing the material present. Cavity 218 may also create certain controlled configurations of the distal tip when the distal tip is engaged with the distal stop 214. Cavity 218 may cause soft body portion 208 to accordion when balloon catheter 200 is advanced to distal tip 214. This may help the balloon catheter to push off from distal stop 214 more gradually. Cavity 218 may also be configured so that when balloon catheter 200 is advanced to distal tip 214, the distal portion of the distal tip inverts and extends inside the cavity as shown in FIG. 4, which is a partial cross-sectional view of the embodiment of FIG. 3. In this case, the energy stored in the deformed tip will help to peel the tip off distal stop 214. The process of the distal tip reverting to its unstressed state and returning to a state of less stored energy may provide a superior tactile feel to the operator of the balloon catheter.

FIG. 5 is a cross-sectional view depicting another example embodiment. In this embodiment, a distal tip 306 is molded so that the distal end is pre-configured to be in an inverted position. Distal tip 306 includes a soft body portion 308 which extends distally and then inverts to extend proximally into a cavity 318. A rigid ring 310 is provided at the end of the inverted portion. This embodiment provides for less possible elastic deformation of the distal tip which may be advantageous to further reduce intravascular vessel trauma, for example. This embodiment, nevertheless, provides for a configuration in which the distal tip is more readily removable than a standard distal tip. For example, this embodiment may be readily removed from a distal stop through a peeling action, in which the inverted portion tends to move to a more distal, non-inverted configuration.

Figure 6:
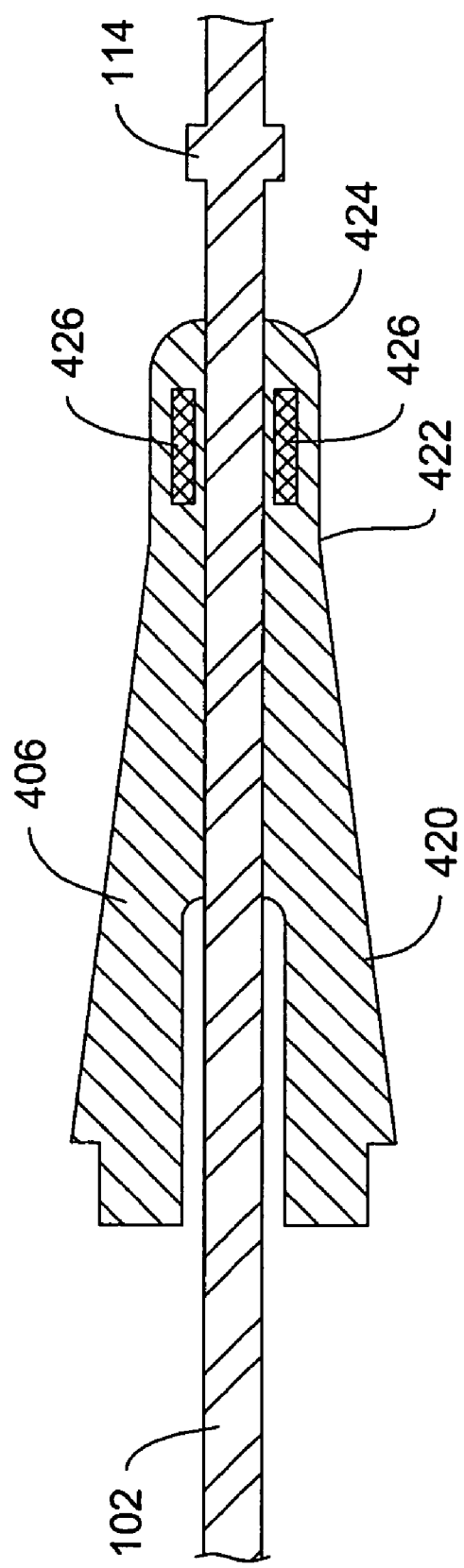
FIG. 6 is a diagrammatic cross-sectional view of an example distal tip.

FIG. 6 is a diagrammatic cross-sectional view of another example embodiment of a distal tip 406. Distal tip 406 is shown disposed on a guidewire 102 having a distal stop 114 and has an inner diameter such that it slidably fits over the guidewire. Distal tip 406 may have a gradual taper 420 down to diameter 422 and then may include a sharper final taper 424. Diameter 422 may extend for a distance or may be the transition point between taper 420 and taper 424. Final taper 424 is at the distal-most end of tip 406 and may be a radius or a bevel. Final taper 424 may make it harder to push tip 406 over stop 114 on guidewire 102. Final taper 424 may be formed by reflow of distal tip 406 or other suitable process. Distal tip 406 may include other elements described above, such as a marker band 426, or a rigid ring, just proximal the final taper. Distal tip 406 with marker band 426 embedded within may be produced using any suitable process. For example, marker band 426 may be inset molding molded within distal tip 406. In another example method of manufacture, a distal tip precursor may be molded with a groove sized and positioned for a marker band. The groove may have a distal facing opening, or other suitable opening. A marker band may then be inserted into the distal tip precursor. The distal tip precursor may then be selectively remolded into a distal tip 406 by selective reflowing. The reflowing may be accomplished through any suitable method, such as localized application of thermal or laser heating. Embodiments are contemplated where marker band 426 is distal or proximal the location shown in FIG. 6.

The rings of the several embodiments may be any element suitable to prevent the distal end from stretching when the distal end of the medical device encounters a distal stop on a guidewire. A ring may, for example, be an annular metal ring formed from a wire, formed from a hypotube, or machined. A ring may be affixed to a distal tip through adhesive, fusing, or other suitable process or may be molded into the distal tip. A ring may include stainless steel, nitinol, or other suitable metal able to withstand the forces applied without breaking. If desired, a ring may include materials such as platinum, iridium, tantalum, or gold, or suitable alloys to make the tip more radiopaque. A ring may alternatively be a suitable coil resistant to radial distention. A ring may also be made from a suitable polymer such as a thermoplastic or resin. The ring may be machined or molded into the desired shape and may be adhesively affixed or molded into the distal tip. A ring may include anchoring sites such as circular, star-shaped, or other suitably shaped holes or protrusions to create better attachment between the ring and the rest of the distal tip. A ring may be a locally crystallized portion of an elastomer distal tip. A ring may also be formed from deposition of a rigid material, such as metal, onto the distal tip.

The soft body portion of the several embodiments may be made from any suitably soft and elastic material such as certain polymers. The material of a soft body portion and the material of a ring may be selected with a view towards good adhesion between the two. A distal tip may also include a tie layer between the soft body portion and the ring. A soft body portion should be flexible and resistant to tearing. For example, one suitable polymer may be selected from the group of polyether-block co-polyamide polymers. The inner and outer surfaces of a distal tip may be given a lubricious coating. This may be done, for example, with a polytetrafluoroethylene polymer.

It should be understood that this disclosure is, in many respects, only illustrative. Numerous advantages of the invention covered by this document have been set forth in the foregoing description. Changes may be made in details, particularly in matters of shape, size and arrangement of parts without exceeding the scope of the invention. Those of skill in the art will readily appreciate that other embodiments may be made and used which fall within the scope of the claims attached hereto. The invention's scope is, of course, defined in the language in which the appended claims are expressed.

What is claimed is:

1. A medical device comprising:
a guidewire having a first diameter and a distal stop having a second diameter greater than the first diameter;
an elongate tubular member having a proximal end and a distal end with a guide wire receiving lumen extending therethrough, a distal portion of the guidewire lumen having an inner diameter of substantially the same magnitude as the first diameter; and
a tip disposed at the distal end of the elongate tubular member and having a distal end, a proximal end and a tip lumen therethrough, the tip having an elastic portion and a radially inextensible distal portion distal of the elastic portion;

wherein the elongate tubular member is slidably disposed on the guidewire such that the distal end of the tip engages against the distal stop when the elongate tubular member is advanced distally relative to the guidewire;

wherein the tip comprises an amorphous polymer and the radially inextensible distal portion comprises a locally crystalline section thereof;

wherein the radially inextensible distal portion is a distal-most extremity;

wherein when the tip directly contacts the distal stop and the elongate tubular member is forced distally relative to the guidewire, the elastic portion of the tip inverts inwardly and the radially inextensible distal portion enters an internal cavity within the tip.

2. The medical device of claim 1, wherein the radially inextensible distal portion comprises a ring having a lumen therethrough.

3. The medical device of claim 1, wherein the radially inextensible distal portion is machined.

4. The medical device of claim 1, wherein the radially inextensible distal portion is formed by deposition.

5. The medical device of claim 1, wherein the radially inextensible distal portion comprises a non-compliant plastic band.

6. The medical device of claim 1, wherein the elastic portion tapers from a first outer diameter at a first location along the tip to a second outer diameter less than the first outer diameter at a second location along the tip distal of the first location.

7. The medical device of claim 6, wherein at the first location along the tip, the tip has a first thickness and a first inner diameter, and wherein at the second location along the tip distal of the first location, the tip has a second thickness less than the first thickness and a second inner diameter greater than the first inner diameter.

8. The medical device of claim 7, wherein the elastic portion comprises an inner surface concave in a first plane normal to a longitudinal axis and a second plane normal to the first plane.

9. The medical device of claim 1, wherein the tip lumen further comprises a cavity within the tip, wherein the cavity forms a concave hollow that is larger in diameter than the inner diameter of the guidewire lumen.

10. A medical device comprising:
a guidewire having a first diameter and a distal stop having a second diameter greater than the first diameter;
an elongate amorphous polymeric tubular member having a proximal end, a distal end, and a guidewire lumen extending therethrough, wherein a distal portion of the guidewire lumen has an inner diameter of substantially the same magnitude as the first diameter; and
an integrally formed tip disposed at the distal end of the elongate tubular member and having a distal end, a proximal end, a tip lumen extending therethrough in fluid communication with the guidewire lumen, and an enlarged cavity formed within the tip lumen between the proximal end and the distal end of the tip;
wherein the tip includes an elastic portion disposed immediately proximal a radially inextensible distalmost extremity comprising a locally crystalline section thereof;
wherein the elongate amorphous polymeric tubular member is slidably disposed on the guidewire such that the distal end of the tip engages against the distal stop when the elongate tubular member is advanced distally along the guidewire;
wherein when the tip directly contacts the distal stop and the elongate tubular member is forced distally relative to the guidewire, the elastic portion of the tip inverts inwardly and the radially inextensible distalmost extremity enters the enlarged cavity within the tip.

11. The medical device of claim 10, wherein the inverted tip stores energy that is released when the tip returns to an everted state, and the stored energy assists in peeling the tip off of the distal stop.

12. The medical device of claim 11, wherein releasing the stored energy provides tactile feedback to an operator of the medical device.

* * * * *